United States Patent [19]

Freeman

[11] Patent Number: 5,205,284
[45] Date of Patent: Apr. 27, 1993

[54] METHOD AND APPARATUS FOR TRANSCUTANEOUS ELECTRICAL CARDIAC PACING WITH BACKGROUND STIMULATION

[75] Inventor: Gary A. Freeman, Newton Center, Mass.

[73] Assignee: Zoll Medical Corporation, Woburn, Mass.

[21] Appl. No.: 537,069

[22] Filed: Jun. 12, 1990

[51] Int. Cl.$^5$ .............................................. A61N 1/368
[52] U.S. Cl. ............................ 128/419 PG; 128/421
[58] Field of Search ............. 128/419 PG, 419 D, 421

[56] References Cited

U.S. PATENT DOCUMENTS

| | | | |
|---|---|---|---|
| 2,558,270 | 6/1951 | Reiter | 128/428 |
| 2,590,876 | 4/1952 | Landauer | 128/417 |
| 2,771,554 | 11/1956 | Gratzl | 250/27 |
| 2,864,371 | 12/1958 | Parodi | 128/415 |
| 2,915,066 | 12/1959 | Parodi | 128/419 |
| 3,024,783 | 3/1962 | Timcke | 128/2 |
| 3,050,695 | 8/1962 | Du Vall | 331/52 |
| 3,077,884 | 2/1963 | Batrow et al. | 128/423 |
| 3,645,267 | 2/1972 | Hagfors | 128/421 |
| 3,731,111 | 5/1973 | Charters | 307/106 |
| 3,817,254 | 6/1974 | Maurer | 128/421 |
| 3,888,261 | 6/1975 | Maurer | 128/420 |
| 4,014,347 | 3/1977 | Halleck et al. | 128/422 |
| 4,147,171 | 4/1979 | Greene et al. | 128/421 |
| 4,177,817 | 12/1979 | Bevilacqua | 128/802 |
| 4,210,151 | 7/1980 | Keller, Jr. | 128/421 |
| 4,237,899 | 12/1980 | Hagfors et al. | 128/422 |
| 4,331,157 | 5/1982 | Keller, Jr. et al. | 128/419 |
| 4,349,030 | 9/1982 | Belgard et al. | 128/419 |
| 4,723,536 | 2/1988 | Rauscher et al. | 128/1.5 |

FOREIGN PATENT DOCUMENTS

0314078 3/1989 European Pat. Off.
1350016 4/1974 United Kingdom.

OTHER PUBLICATIONS

Goovaerts et al., "A General-Purpose Microprocessor System for Medical Instrumentation and Electrical Stimulation", J. Biomed Eng., vol. 6, pp. 90–96 (Apr. 1984).

Geddes, "A Short History of the Electrical Stimulation of Excitable Tissue Including Electrotherapeutic Applications", Supp. to The Physiologist, vol. 27, No. 1 (Feb. 1984).

Eriksson et al., "Hazard From Transcutaneous Nerve Stimulation in Patients With Pacemakers", The Lancet, p. 1319 (Jun. 17, 1978).

Geddes et al., "Electroventilation", American Journal of Emergency Medicine, vol. 3, No. 4, pp. 338–339 (Jul. 1985).

Rosenbaum et al., "Simple Cardiac Pacemaker and Defibrillator", The Journal of American Medical Association, vol. 155, No. 13, p. 1151 (1954).

Schechter, "Background of Clinical Cardiac Electrostimulation; IV. Early studies on feasibility of accelerating heart rate by means of electricity", New York State Journal of Medicine, pp. 395–404 (Feb. 1972).

Kahn et al., "Technical Aspects of Electrical Stimulation Devices", Med. Progr. Technol., vol. 1, No. 2, pp. 58–68 (1972).

Schechter, "Background of Clinical Cardiac Electrostimulation; III. Electrical regulation of rapid cardiac dysrhythmias", New York State Journal of Medicine, pp. 270–284 (Jan. 15, 1972).

Schechter, "Background of Clinical Cardiac Electrostimulation; VII. Modern era of artificial cardiac pacemakers", New York State Journal of Medicine, pp. 1166–1190 (May 15, 1972).

(List continued on next page.)

Primary Examiner—William E. Kamm
Assistant Examiner—Scott M. Getzow
Attorney, Agent, or Firm—Fish & Richardson

[57] ABSTRACT

Method and apparatus for transcutaneously pacing the heart with background stimuli occurring in the intervals between pacing stimuli to reduce patient discomfort during pacing.

29 Claims, 6 Drawing Sheets

OTHER PUBLICATIONS

Goovaerts et al., "A Programmable Stimulator for Physiological Applications", Medical and Biomedical Engineering, pp. 112–118 (Jan. 1975).

Furman et al., "Pulse Duration Variation and Electrode Size as Factors in Pacemaker Longevity", The Journal of Thoracic and Cardiovascular Surgery, vol. 69, No. 3, pp. 382–389 (Mar. 1975).

Fisher et al., "Termination of Ventricular Tachycardia With Bursts of Rapid Ventricular Pacing", The American Journal of Cardiology, vol. 41, pp. 94–102 (Jan. 1978).

"A New Approach to Pain", reprinted from Emergency Medicine (Mar. 1974).

Ritchie et al., "A Simple Variable 'Square-Wave' Stimulator for Biological Work", vol. 21, pp. 64–65 (Apr. 1944).

Schechter, "Background of Clinical Cardiac Electrostimulation; VI. Precursor apparatus and events to the electrical treatment of complete heart block", New York State Journal of Medicine, pp. 953–961 (Apr. 15, 1972).

Stimulaton Technology, Inc., Minneapolis, Minn., EPC® Stimulators Brochure.

Cotter, "Overview of Transcutaneous Electrical Nerve Stimulation for Treatment of Acute Postoperative Pain", Medical Instrumentation, vol. 17, No. 4, pp. 289–292 (1983).

Pearce et al., "Myocardial Stimulation with Ultrashort Duration Current Pulses", PACE, vol. 5, pp. 52–58 (1982).

Geddes, "The Beginnings of Electromedicine", IEEE Engineering in Medicine and Biology Magazine, pp. 8–23 (Dec. 1984).

Castillo et al., "Use of Electrical Pacemakers in the Management of Cardiac Arrhythmias", Geriatrics, pp. 117–131.

Tursky et al., "Electrocutaneous Threshold Changes Produced by Electric Shock", Psychophysiology, vol. 7, No. 3, pp. 490–498 (1971).

Hill et al., "Relationship of Electrically Induced Pain to the Amperage and the Wattage of Shock Stimuli," Wattage, Amperage and Pain Stimuli, pp. 464–472 (1952).

W. G. S. Stephens, "The Response of Human Motor Nerve", P.R.S.E., vol. LXX, B, pp. 49–61 (1966–1967).

Cook, "Effects of low frequency stimulation on the monosynaptic reflex (H reflex) in man", Neurology, vol. 18, pp. 45–51 (1968).

Jeneskog, "Cutaneous inhibition of high threshold muscle afferent pathways", Acta Physiol Scan, 107: 297–308 (1979).

"Cardiac Arrest and Ventricular Fibrillation", McMillan, I. K. R., et al., J. Thorax, vol. VII, 1952.

Physiology & Biophysics, Theodore C. Ruch, Ph.D & Harry D. Patton, Ph.D, M.D., W. A. Saunders Company, Philadelphia and London, 1964.

"Clinical experience and problems encountered with an implantable pacemaker," Morris, J. D. et al., J. Thoracic Cardiovascular Surgery, vol. 50, No. 1, 1965.

Control of Heart Action by Electrical and Mechanical Means, Paul M. Zoll & Arthur J. Linenthal, Year Book Medical Publishers, Inc., Chicago, Sep. 1966.

Physical Aspects of Artifical Heart Stimulation, Hans Schneider, Drukkerij Elinkwijk, Utrecht, 1966.

"Measurement of the pain threshold determined by electrical stimulation and its clinical application" Notermans, S. L. H., Neurology, pp. 1071–1086, 1966.

Cardiac Pacemakers, H. Siddons & E. Sowton, Charles C. Thomas, Springfield, 1967.

Principles of Apllied Biomedical Instrumentation, L. A. Geddes & L. E. Baker, John Wiley & Sons, New York, London, 1968.

"Historical Development of Cardiac Pacing," Paul Zoll, MCV/Q, vol. 7, No. 4, 1971.

Electrogenesis and Contractility in Skeletal Muscle Cells, Jozef Zachar, Publishing House of the Slovak Academy of Sciences, Bratislava, 1971.

Abstracts, The Journal of Emergency Medicine, vol. 6, No. 1, pp. 79–83, 1988.

"Improving Pacemaker Electrodes," Cardiac Pacing: Proceedings of the IVth International Symposium On Cardiac Pacing, H. J. Thalen, Ed., 1973.

"Transcutaneous Nerve Stimulation for Control of Pain," C. Norman Shealy et al., Surg. Neurol., vol. 2, Jan. 1974.

"Optimal Stimulus Parameters for Minimum Pain in the Chronic Stimulation of Innervated Muscle," F. Gracanin et al., Arch Phys. Med. Rehabil., vol. 56, Jun. 1975.

"Pacemaking and Ventricular Fibrillation," M. Jones, B.S. and L. A. Geddes, M.E., Ph.D, Cardiovascular Research Bulletin, vol. 15, No. 4, 1977.

OTHER PUBLICATIONS

Impedance Measurements In Biological Cells, Otto F. Schanne & Elena Ruiz P.-Ceretti, A Wiley-Interscience Publication, John Wiley & Sons, New York, 1977.

"Comparative efficacy of damped sine wave and square wave current for transchest ventricular defibrillation in animals," J. D. Bourland et al., Medical Instrumentation, vol. 12, No. 1, 1978.

"Tissue stimulation: theoretical considerations and practical applications," L. A. Geddes & J. D. Bourland, Med. & Biol. Eng. & Comput., vol. 23, No. 2, pp. 131–137, 1985.

"Choice of the Optimum Pulse Duration for Precordial Cardiac Pacing: A Theoretical Study," L. A. Geddes, et al, Pace, vol. 8, 1985.

"Transcutaneous Electrical Nerve Stimulators," American National Standard, Association for the Advancement of Medical Instrumentation, 1986.

TextBook of Medical Physiology, Arthur C. Guyton, M.D., W. B. Saunders Company, 1980.

"Symmetrical Biphasic TENS Waveform for Treatment of Back Pain," Jerry Lampe and Bill Dunn, The Clinical Journal of Pain, vol. 3, No. 3, 1987.

"Minimizing Cutaneous Pain During Electrical Stimulation," IEEE: 9th Annual Conference of The Engineering in Medicine and Biology Society, IEEE 1987.

"Suggested Electrode Placement Patterns Using Nuwave and Lo-back Electrodes," Staodyn, Inc., 1988.

Computerized EMG Monitoring In Anesthesia And Intensive Care, Harvey L. Edmonds, Jr. Ph.D., et al., Instrumentarium Science Foundation, Malherbe Publishing Corp., the Netherlands, 1988.

"Modified impulse diminishes discomfort of transcranial electrical stimulation of the motor cortex," Josef Zentner et al., Electromyogr. Clin. Neurophysiol., 29, pp. 93–97, 1989.

"A Comparative Study of Five Transcutaneous Pacing Devices in Unanesthetized Human Volunteers," Michael B. Heller, MD et al., Prehospital and Disaster Medicine, Jul.–Sep., 1989.

METHOD AND APPARATUS FOR TRANSCUTANEOUS ELECTRICAL CARDIAC PACING WITH BACKGROUND STIMULATION

BACKGROUND OF THE INVENTION

This invention relates to electrically pacing the heart transcutaneously.

During transcutaneous, or external, electrical pacing of a patient's heart, electrical stimuli travel from the pacing apparatus' electrodes to the heart through the patient's skin and skeletal thorax muscles to stimulate the heart. Depending on the magnitude of the stimuli and the characteristics of a particular patient's skeletal muscles, the skeletal muscles may contract in response to the passage of the electrical stimuli through them. Similarly, the passage of the electrical pacing stimuli through the patient's skin may stimulate cutaneous nerves and muscles located near to the skin. This nerve stimulation and skeletal muscle contraction may feel uncomfortable to the patient, or even become painful enough to result in the patient's intolerance of extended transcutaneous heart pacing.

It has been shown (U.S. Pat. No. 4,349,030) that the skeletal muscle contractions and cutaneous nerve stimulation associated with conventional transcutaneous heart pacing may be reduced by lengthening the duration of electrical pacing stimuli to greater than five milliseconds.

SUMMARY OF THE INVENTION

In general, the invention features providing background stimuli in the intervals between pacing stimuli to reduce discomfort during pacing. In preferred embodiments, the background stimuli occur only in the intervals between the pacing stimuli; the background stimuli comprise pulses; the average amplitude of the background pulses is less than the average amplitude of the pacing stimuli; the average amplitude of the background pulses is less than 20 mA (more preferably less than 10 mA); and the duty cycle of the background pulses is less than 80% (more preferably less than 50%).

Other features and advantages of the invention will be apparent from the following description of a preferred embodiment and from the claims.

DESCRIPTION OF THE PREFERRED EMBODIMENT

Figure 1:
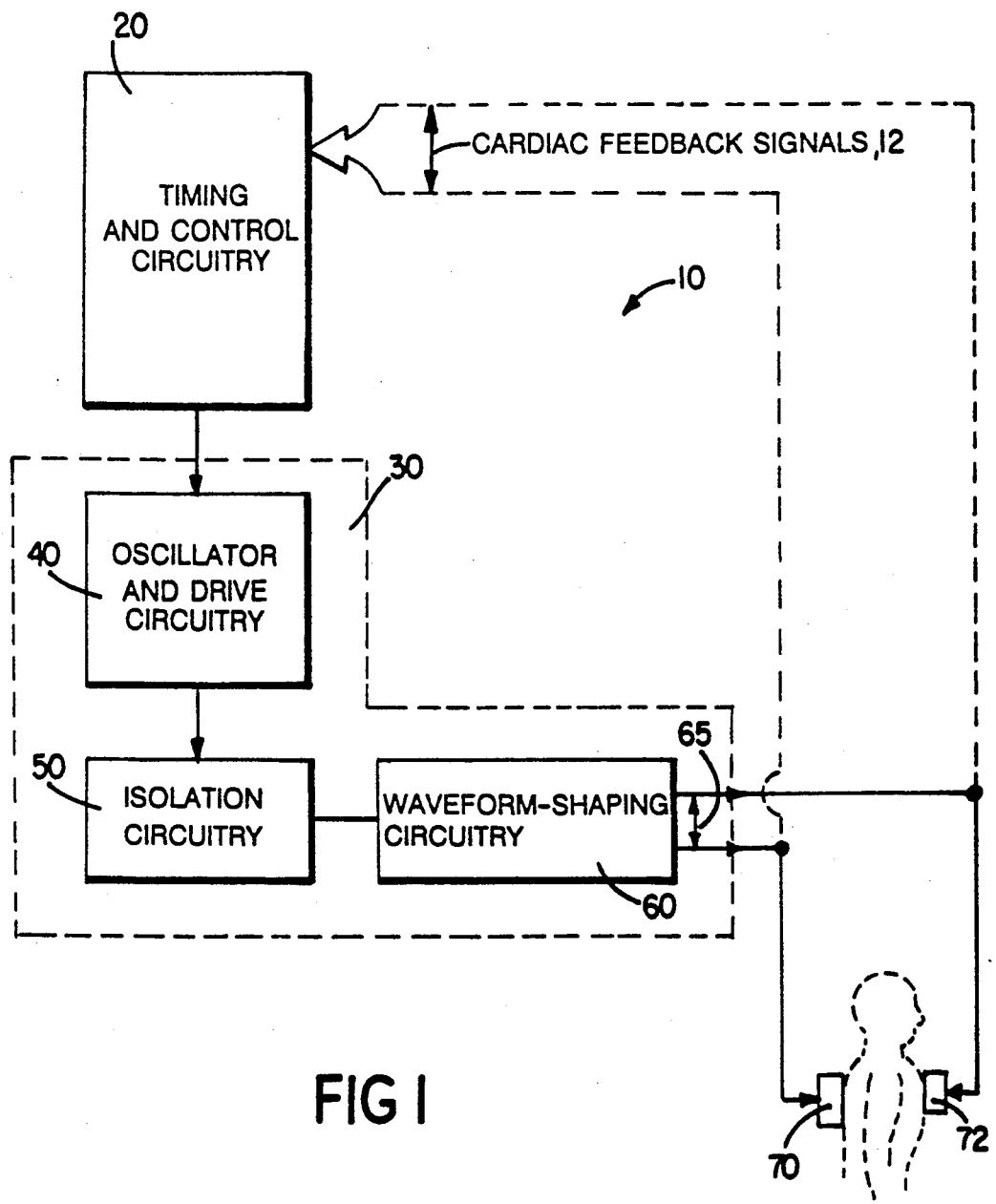
FIG. 1 is a block diagram of a pacing stimuli signal generator according to one embodiment of the invention.

Referring to FIG. 1, there is shown a signal generator 10 for generating electrical pacing stimuli 65 which are to be applied transcutaneously to a patient's heart. The signal generator's timing and control circuitry 20 can accept cardiac feedback signals 12 from the patient to initiate electrical pacing stimuli, or it can operate without such feedback (asynchronous pacing). The timing and control circuitry also sets the timing characteristics of the pacing stimuli, as discussed below. The timing and control circuitry 20 initiates the pacing stimuli by signaling the stimuli generating circuitry 30, which includes oscillator and drive circuitry 40, isolation circuitry 50, and waveform-shaping circuitry 60. Oscillator and drive circuitry 40 generates a stream of pulses that are processed by isolation circuitry 50, which isolates the signal generator's internal voltages from the patient, thereby providing electrical hazard protection for the patient during the patient's exposure to the pacing stimuli 65.

Waveform-shaping circuitry 60 receives the isolation circuitry's pulse stream output and modifies signal characteristics of the pulse stream, e.g., pulse shape, polarity, and amplitude, to generate pacing stimuli 65 having user-specified signal parameters. At the signal generator's output, the pacing stimuli 65 are coupled to posterior and anterior electrodes 70, 72, which together externally deliver the electrical stimuli to the patient for transcutaneous pacing of the patient's heart.

Figure 2:
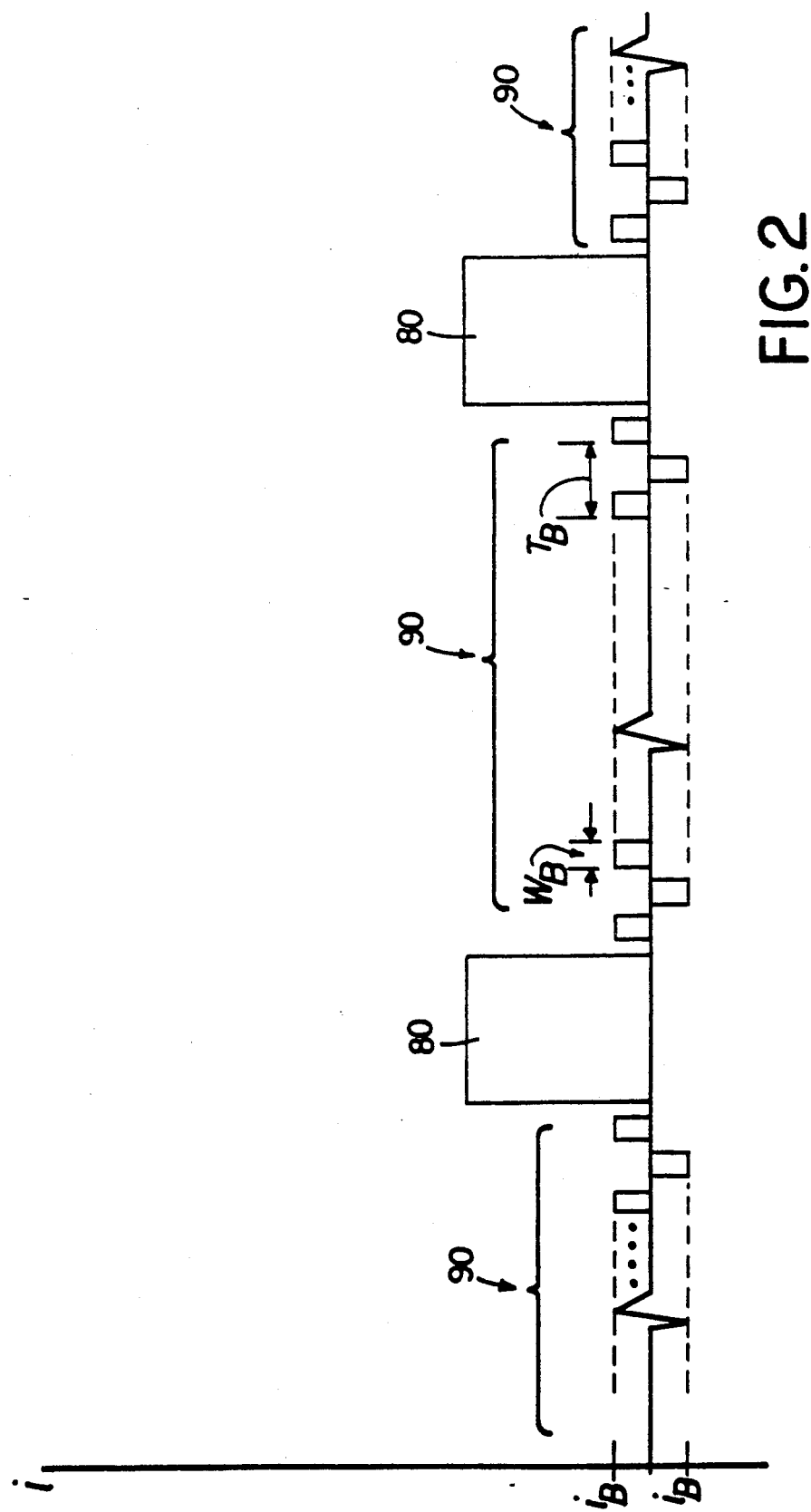
FIG. 2 is an illustrative example of electrical stimuli produced by the signal generator of FIG. 1.

Referring to FIG. 2, the signal generator's electrical pacing stimuli output 65 is composed of pacing stimuli 80 and background pulse trains 90. The pacing stimuli 80, comprising, for example, pacing pulse trains, are delivered to the patient to stimulate the patient's heart. The background pulse trains 90 are delivered to the patient in the intervals between the pacing pulse trains, when the heart is not being stimulated. Together, these pulse train stimuli provide effective transcutaneous stimulation of the heart with reduced patient discomfort.

Figure 3A:
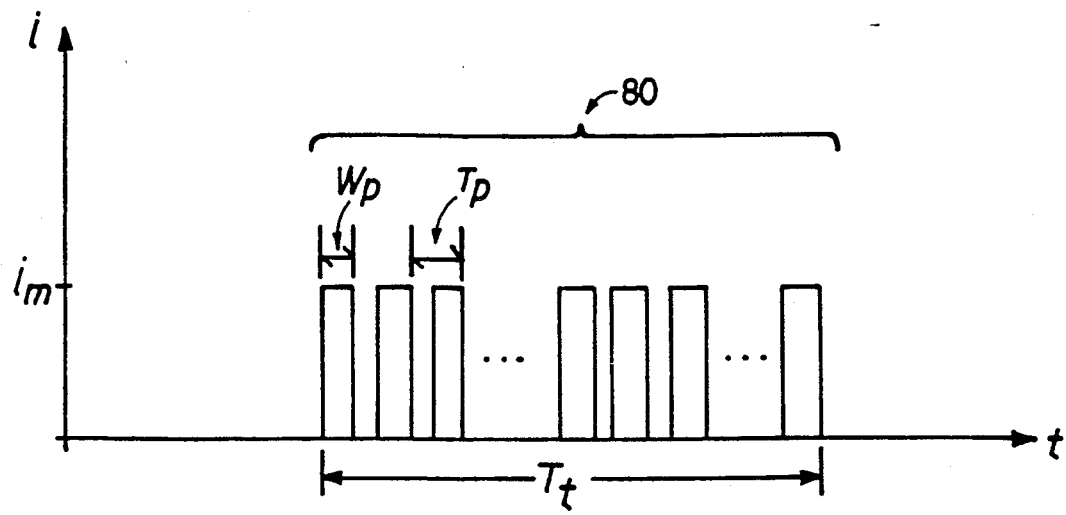
FIGS. 3A and 3B are illustrative examples of electrical pacing stimuli produced by the signal generator of FIG. 1.

Referring to FIG. 3A, the pacing pulse trains 80 each consist of a series of pulses, with each pulse having a time duration, or width, $W_p$, which may be different than the duration of the other pulses in the series.

Figure 3B:
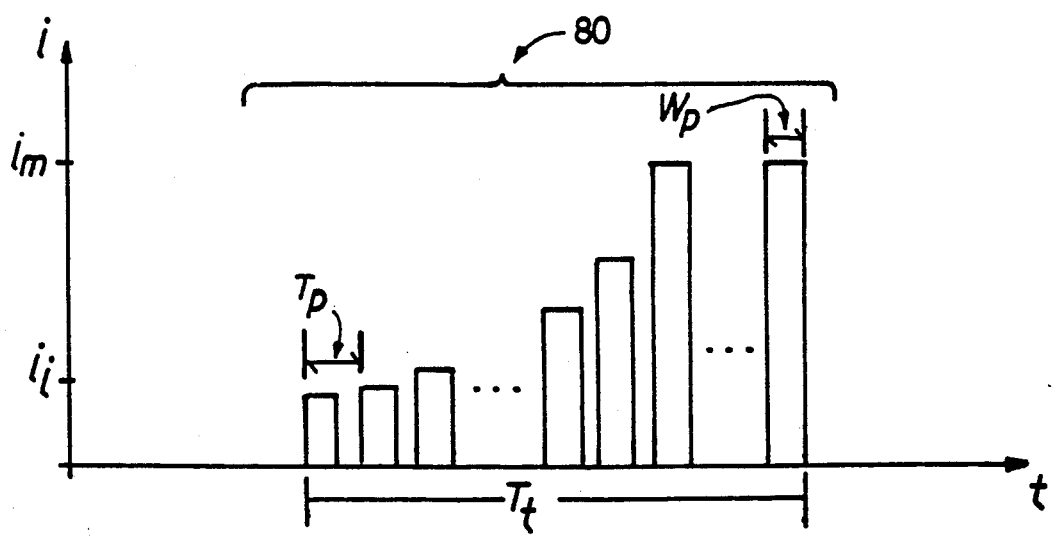
Figure 4:
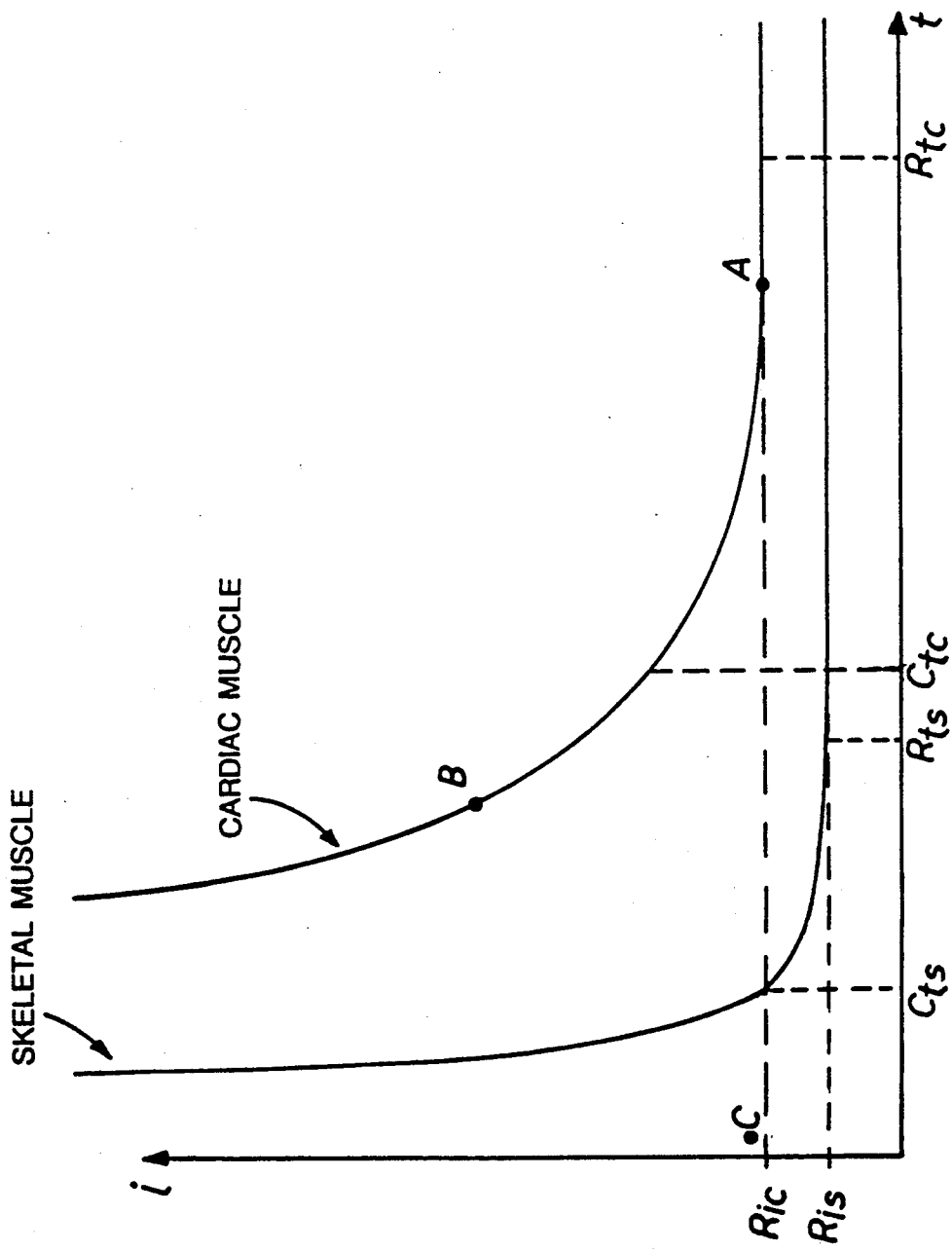
FIG. 4 are plotted characteristics, one for cardiac muscle and one for skeletal muscle and cutaneous nerves, relating a stimulating pulse's strength with the pulse's duration.

Referring also to FIG. 4, there are shown characteristic curves for pulse stimuli, representing the relationship between a pulse's current amplitude, or strength, i, and a pulse's duration, t, for stimulating cardiac muscle and skeletal muscle. The duration, $T_t$, of each pacing pulse train 80 (FIG. 3) is chosen by considering these strength-duration curves. Each curve delineates the minimum duration, t, which an electrical pulse stimulus having a given current amplitude, i, will require to stimulate a muscle. Stated another way, given a pulse amplitude, i, a muscle will not be stimulated unless the pulse duration, t, is on, or to the right of, the corresponding curve. Two different stimulus points lying on the strength-duration curve for a muscle, like points A and B on the cardiac muscle curve, will equally effectively stimulate that muscle.

A minimum pulse amplitude, or rheobase ($Ri_c$ for cardiac muscle and $Ri_s$ for skeletal muscle), defines the smallest pulse amplitude that will stimulate a muscle. Any stimulus having a current amplitude less than the rheobase will not stimulate a muscle, even if the pulse's duration is greater than the rheobase duration, called the utilization time, ($Rt_c$ for cardiac muscle and $Rt_s$ for skeletal muscle). Comparing the strength-duration curves of FIG. 4, the cardiac muscle's utilization time, $Rt_c$, which is greater than approximately 40 msec, is longer than that of skeletal muscle, having a utilization time $Rt_s$ which is considerably less than 40 msec.

Given these utilization times for cardiac and skeletal muscle, a preferable range for the pacing pulse trains' durations $T_t$ is selected with the following consideration. While any stimulus point on the cardiac strength-duration curve produces effective cardiac stimulation, stimulus points having lower current amplitudes tend to produce lower skeletal muscle stimulation than stimulus points having higher current amplitudes, for a given stimulus duration. Accordingly, a pulse stimulus having the characteristics of point A (close to the cardiac utilization time $Rt_c$) stimulates skeletal muscle less than a pulse stimulus having the characteristics of point B, but will stimulate the heart equally effectively. Therefore, by choosing a pulse train duration around the same duration as the cardiac utilization time, the heart can be adequately stimulated by the pulse train while producing less skeletal muscle stimulation than would be produced by a pulse train of shorter duration and correspondingly higher pulse current amplitudes. The total time duration, $T_t$, of each pacing pulse train is therefore preferably at least 5 msec, or more preferably 20 msec, but may be of any duration sufficient to stimulate the heart. The maximum preferable pacing pulse train duration is limited to approximately 150 msec because of safety considerations for inducing cardiac fibrillation.

The pulse width $W_p$ and pulse period $T_p$ of each of the pulses in the pacing pulse trains are also selected based on a comparison of the strength-duration relationships for cardiac muscle and skeletal muscle (FIG. 4). As shown in FIG. 4, a minimum pulse duration, called the chronaxie ($Ct_c$ for cardiac muscle and $Ct_s$ for skeletal muscle), is the pulse duration corresponding to a stimulating pulse amplitude equal to twice the rheobase of a muscle. With a pulse stimulus having a duration shorter than the chronaxie, it becomes increasingly difficult to stimulate a corresponding muscle.

Considering the strength-duration curves of FIG. 4, the cardiac muscle's chronaxie $Ct_c$ is approximately equal to 2 msec and the skeletal muscle's chronaxie $Ct_s$ is approximately equal to 0.5 msec. A pulse stimulus of a duration shorter than the skeletal muscle chronaxie $Ct_s$, having, e.g., the duration of a pulse at point C, would therefore tend not to stimulate either cardiac muscle or skeletal muscle. However, a train of such pulses having suitably adjusted amplitudes and a pulse train duration $T_t$ which is longer than the cardiac muscle chronaxie $Ct_c$, e.g., the stimulus duration of point A, effectively stimulates the heart as if the pulse trains had been filtered by, e.g., the skeletal muscles, to produce a continuous pacing pulse.

Referring again to FIG. 3, based on this consideration, the pulse width $W_p$ of each of the pacing pulses is selected to be less, preferably much less, than the skeletal muscle chronaxie $Ct_s$ (0.5 msec). With pulses of such width, the skeletal muscles tend to be stimulated less than they would if the pacing pulse were a single continuous pulse, but the heart is stimulated as effectively as a continuous pulse. The pacing pulse width $W_p$ for achieving this condition is preferably less than 100 microseconds, and most preferably less than 15 microseconds. Pulse widths of less than about 7 microseconds may produce a pacing pulse frequency which is high enough to cause tissue damage, and thus may need to be avoided. Given the selected pulse width $W_p$, the pacing pulse period $T_p$ is selected to ensure adequate pacing stimulation, or capture, of the heart. The preferred pacing pulse duty cycle is 66%, but a lower duty cycle, e.g., 20%, or a variable duty cycle may be used, provided the given duty cycle is adequate to capture the heart. Generally speaking, the higher the duty cycle, the higher will be the effective filtered amplitude of the continuous pulse that influences the cardiac muscle.

A variation in the form of the pacing stimuli is shown in FIG. 3B. The amplitude, $i_i$, of the first pulse in each pacing pulse train has a subthreshold amplitude, i.e., the amplitude is below the minimum pulse amplitude required for stimulation if the pulse amplitude of a given pulse train remained constant for the duration of the pulse train. Each of the pulses following the initial pulse has an amplitude greater than that of the previous pulses, with some number of trailing pulses all having a maximum current amplitude, $i_m$. The value of this maximum current amplitude $i_m$ is selected, along with other pulse train characteristics, e.g., pulse train duration, to ensure capture of the heart. For example, a pulse train with a given number of pulses having a maximum current amplitude $i_m$ may require a shorter duration to capture the heart than a pulse train with fewer pulses having a maximum current amplitude that is greater than $i_m$.

The use of initial, subthreshold pulses, followed by a series of pulses each having an amplitude that is greater than the amplitudes of the preceding pulses is intended to induce accommodation of the skeletal muscles to the pacing pulse train stimuli. Accommodation of a muscle is a physiological phenomenon which can be induced by gradually, rather than abruptly, exposing a muscle to a stimulus amplitude, whereby the stimulating threshold of the muscle is increased beyond the magnitude of the applied stimulus. An accommodated muscle or nerve requires a higher than normal stimulus magnitude to be effectively stimulated, and may even reject stimulation altogether for any magnitude of stimulus increase.

Given the physiological differences between cardiac muscle and skeletal muscle, the amplitudes of the pulses in the pacing pulse train are selected to cause accommodation of skeletal muscles but not to cause accommodation of cardiac muscle. By simultaneously achieving these conditions, the pacing pulse trains effectively stimulate the heart but tend to decrease the skeletal muscle stimulation typically associated with the transcutaneous cardiac muscle stimulation.

Referring again to FIG. 2, the background pulse trains 90 are provided during the intervals between the pacing stimuli. Each background pulse train comprises a series of pulses, with the amplitudes of the pulses alternating between a positive amplitude, $i_B$, and a negative amplitude, $-i_B$, in a biphasic fashion. While FIG. 2 shows each of the background pulses having the same amplitude magnitude, each of the pulses may have differing amplitudes. The magnitude of the alternating amplitudes, $|i_B|$, is preferably below the minimum current amplitude which a pulse, having the width $W_B$, would require to stimulate the skeletal muscles.

During the interval between each background pulse, the background pulse train has an amplitude, e.g., zero amplitude, that is below the current amplitude required to stimulate skeletal muscle. Given a particularly chosen amplitude between pulses, the pulse width $W_B$ and period $T_B$ of the background pulses are chosen to fulfill two criteria: 1. The duty cycle ($100 \times 2W_B/T_B$) of the background pulses is preferably less than 80%, or more preferably less than 50%, for providing a low average current; and 2. For a given $i_B$, $T_B$, and $W_B$ combination, the skeletal muscles are minimally stimulated. The average current ($i_B \times$ duty cycle) is preferably less than 20 mA, and more preferably less than 10 mA.

The subthreshold stimulus from the background pulse trains 90 tends to reduce the pacing pulse trains' stimulation of the skeletal muscles, possibly through accommodation of those muscles. That is, by adding the background pulse trains, the discomfort from stimulation of skeletal muscle during cardiac pacing is less than it would be without the background pulses (when the pacing stimuli are at threshold).

Given the physiological differences between cardiac muscle and skeletal muscle, the background pulse characteristics are accordingly selected to enhance accommodation of the skeletal muscles while discouraging accommodation of the cardiac muscle. Preferably, the background pulse characteristics are selected to induce a level of skeletal muscle accommodation which increases the muscle stimulation threshold above the largest pacing pulse train stimuli amplitude. The background pulse trains 90, together with the pacing pulse trains 80, thereby tend to produce reduced stimulation of the skeletal muscles while simultaneously achieving effective stimulation of the heart.

The background pulse trains and pacing pulse trains also decrease the cutaneous nerve stimulation associated with transcutaneous cardiac pacing. Because the skeletal muscles and cutaneous nerves have similar chronaxies (FIG. 4), the cutaneous nerves, like skeletal muscles, tend to be stimulated less by the pulses in the pacing pulse trains than they would if the pacing pulse were a single continuous pulse. Furthermore, the background pulse train characteristics selected to produce accommodation of skeletal muscles accordingly produce accommodation of cutaneous nerves.

Referring again to FIG. 1, the signal generator's waveform-shaping circuitry 60 modifies the stream of pulses generated by the oscillator circuitry 40 to create and distinguish the pacing and background pulse trains in the pacing stimuli 65. This modification may require amplitude or polarity adjustment for the particular electrodes used with the signal generator, as discussed below. The timing and control circuitry 20 provides further fine adjustment of the pacing pulse train characteristics, for example, pulse shape. Both the waveform-shaping circuitry 60 and the timing and control circuitry 20 may be programmed to include or omit any or more of the electrical signal characteristics discussed above.

In view of the reduced skeletal muscle and cutaneous nerve stimulation that is achieved by the pacing and background stimuli, the contribution of the electrode configuration to stimulation reduction may be less important. Thus, conventional noninvasive pacing electrodes with nonmetallic skin-contacting members, such as those disclosed in U.S. Pat. No. 4,349,030, or as sold by R-2, of Morton Grove, Illinois, Physio-Control Corporation, of Redmond, Washington, or ZMI Corporation, of Woburn, Massachusetts, are suitable for delivering the pacing pulse trains. Alternatively, electrodes having metallic skincontacting members may be adapted to deliver the pacing stimuli.

Figure 5A:
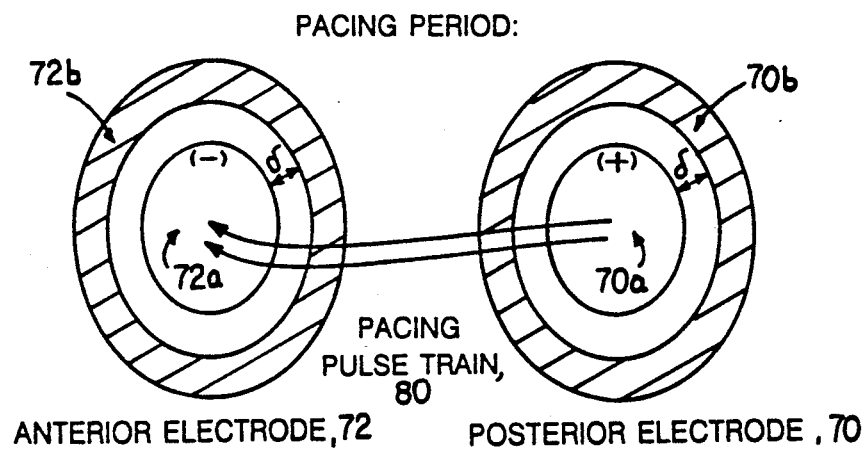
FIGS. 5A and 5B are examples of an electrode configuration for applying the electrical stimuli of FIG. 2 to a patient.
Figure 5B:
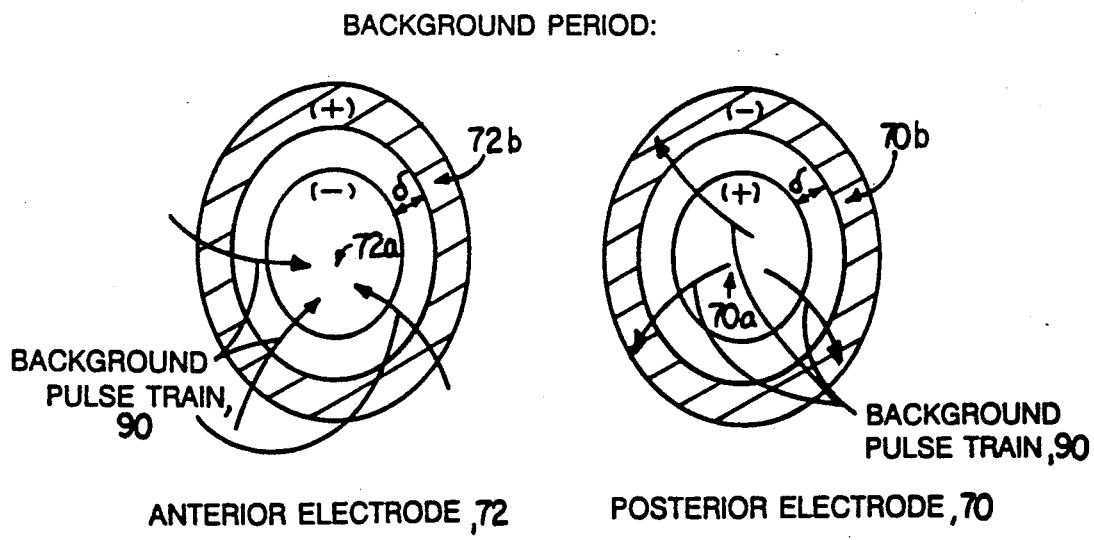

Another suitable electrode configuration is shown in FIG. 5. The anterior electrode 72 and posterior electrode 70 are adapted to deliver the pacing stimuli 65 from the signal generator 10 to a patient. A variety of electrode structures may be adequately used to achieve this function. Preferably, the electrodes are configured so that pacing pulse trains are delivered through the skin and skeletal muscles to the heart, whereas background pulse trains, if existent, are delivered only to the skin and skeletal muscles, and not to the heart. This electrode configuration ensures that cardiac fibrillation will not be induced by the background pulse trains.

As shown in FIG. 5, in this configuration, the electrodes 70, 72 are divided into central, isolated regions 70a, 72a, and surrounding annular regions 70b, 72b. Each of the central regions is separated from its corresponding annular region by a distance which is adequate to provide electrical isolation between the two regions, e.g., at least one-quarter inch. The lateral region within this separating distance may be filled with an adhesive to act as an insulating material between the inner and outer electrode regions.

During delivery of a pacing pulse train, or the "pacing period," the stimuli are passed through the patient's thorax from the posterior electrode's central region 70a to the anterior electrode's central region 72a. During delivery of a background pulse train, or the "background period," the pacing stimuli never pass through the patient, but instead pass between the central and annular regions of each electrode, as shown in FIG. 5. The polarity of, or direction in which, the background stimuli are applied to the patient through the electrodes may be suitably altered without decreasing the effectiveness of the pacing stimuli for pacing the patient's heart. If no background pulse trains are present, the entire stimuli may pass through the patient's thorax from one central region 70a (anode) to the other central region 72a (cathode).

Other embodiments of the invention are within the claims. For example, the background pulses could be used with conventional continuous pacing pulses, and could be applied continuously (even during the pacing stimuli). The background pulses could be monophasic. Individual background pulses could have non-rectangular shapes, e.g., triangular, exponential, or rounded. The amplitude, duration, and duty cycle of the background pulses could vary over time. Gaps could be present in the train of background pulses.

Other variations in the embodiments are disclosed in my copending application Method and Apparatus for Transcutaneous Electrical Cardiac Pacing, Ser. No. 07/536,968 filed on even date herewith (hereby incorporated by reference).

Figure 6A:
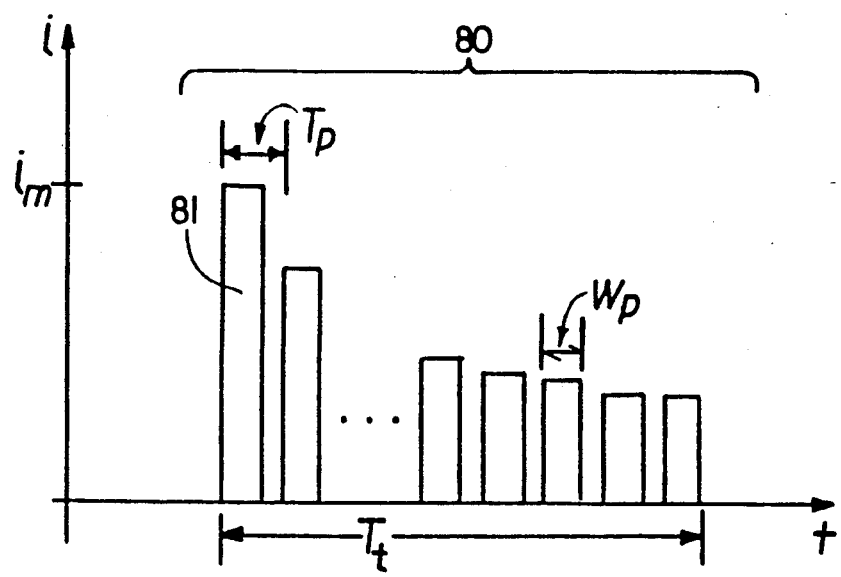
FIGS. 6A–6C are three illustrative examples of alternative pacing stimuli produced by the signal generator of FIG. 1.
Figure 6B:
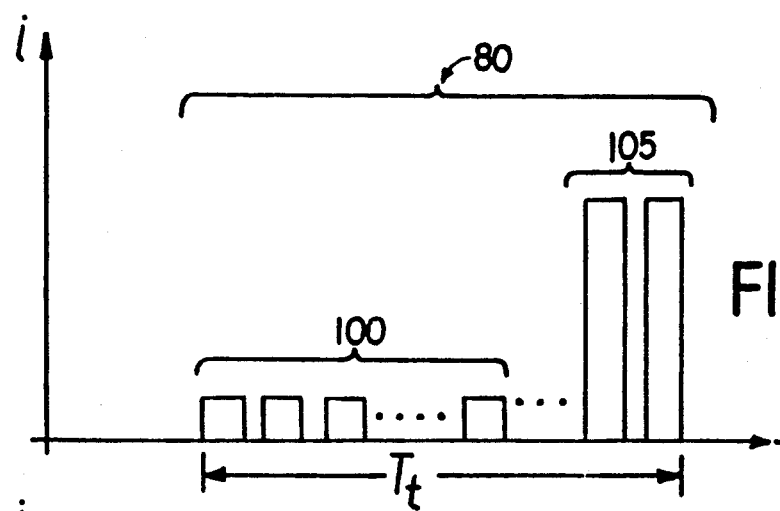
Figure 6C:
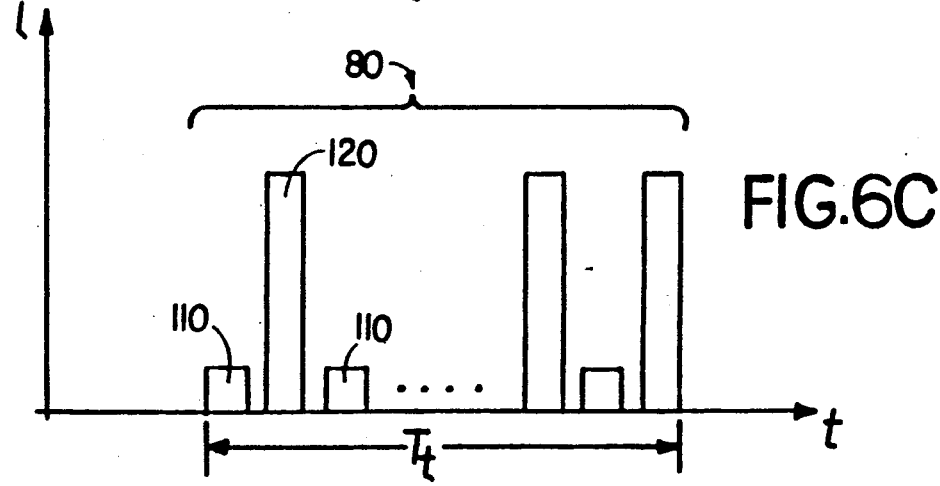

For example, referring to FIG. 6A, the pacing pulse train could have an initial pulse 81 with a maxium amplitude $i_M$, followed by a series of pulses which each has an amplitude that is less than the amplitudes of all preceding pulses. As shown in FIG. 6B, the pacing pulse train could have an initial portion 100 of subthreshold pulses, all of an equal amplitude, followed by a portion 105 of above-threshold pulses, all of an equal amplitude. The initial portion 100 of subthreshold pulses may include a second portion of subthreshold pulses, all of a second, equal amplitude. Alternatively, as shown in FIG. 6C, the pacing pulse train could have alternating subthreshold pulses 110 and above threshold pulses 120. Another variation for achieving the subthreshold pulses is to vary the duration of the pulses, using shorter durations for the subthreshold pulses, and longer durations for the above-threshold pulses. Given any pulse combination in a pacing pulse train, the pulses in a train could have non-rectangular shapes, e.g., triangular, exponential, or rounded. The duty cycle and duration of pulses can be varied within the pulse train (e.g., there could be brief gaps in the sequence of pulses).

What is claimed is:

1. Apparatus for transcutaneously pacing the heart of a patient at a pacing rate, the apparatus comprising
    stimuli generating circuitry means having an output for generating electrical stimuli, and
    electrodes connected to the output of the stimuli generating circuitry means for delivering the electrical stimuli to the patient,
    wherein said stimuli generated and delivered to the patient include
    pacing stimuli occurring generally at the pacing rate, and having a shape and amplitude capable of causing contractions of the cardiac muscle, and
    background stimuli occurring at times other than said pacing stimuli, and having a shape and amplitude incapable of causing contractions of the cardiac muscle.

2. The apparatus of claim 1 wherein said background stimuli occur only at times other than said pacing stimuli.

3. The apparatus of claim 1 wherein each said background stimulus comprises a series of background pulses.

4. The apparatus of claim 3 wherein each said pacing stimulus comprises a series of pacing pulses.

5. The apparatus of claim 4 wherein the average amplitude of said background pulses is less than the average amplitude of said pacing stimuli.

6. The apparatus of claim 5 wherein the duty cycle of said background pulses is less than 80%.

7. The apparatus of claim 6 wherein said duty cycle is less than 50%.

8. The apparatus of claim 5 wherein said series of background pulses has an average current amplitude of less than 20 mA.

9. The apparatus of claim 8 wherein said series of background pulses has an average current amplitude of less than 10 mA.

10. The apparatus of claim 6 wherein each series of pulses is capable, as a group, of causing a contraction of the heart, but each individual pulse is incapable, by itself, of causing such a contraction.

11. The apparatus of claim 10 wherein the duration of the individual pacing pulses averages less than 0.5 msec.

12. The apparatus of claim 11 wherein the duty cycle of said individual pulses is at least 20%.

13. The apparatus of claim 11 wherein the amplitudes of said series of individual pacing pulses rise from a first amplitude to a second amplitude.

14. A method of transcutaneously pacing the heart at a pacing rate, the method comprising the steps of:
    generating electrical stimuli;
    delivering the stimuli to a patient through electrodes applied to the patient's chest;
    wherein the stimuli generated and delivered to the patient include
    pacing stimuli occurring generally at the pacing rate, and having a shape and amplitude capable of causing contractions of the cardiac muscle, and
    background stimuli occurring at times other than said pacing stimuli, and having a shape and amplitude incapable of causing contractions of the cardiac muscle.

15. The method of claim 14 wherein said background stimuli occur only at times other than said pacing stimuli.

16. The method of claim 14 wherein each said background stimulus comprises a series of background pulses.

17. The method of claim 19 wherein each said pacing stimulus comprises a series of pacing pulses.

18. The method of claim 17 wherein the average amplitude of said background pulses is less than the average amplitude of said pacing stimuli.

19. The method of claim 18 wherein the duty cycle of said background pulses is less than 80%.

20. The method of claim 18 wherein said duty cycle is less than 50%.

21. The method of claim 18, wherein said series of background pulses has an average current amplitude of less than 20 mA.

22. The method of claim 21 wherein said series of background pulses has an average current amplitude of less than 10 mA.

23. The method of claim 19 wherein each series of pulses is capable, as a group, of causing a contraction of the heart, but each individual pulse is incapable, by itself, of causing such a contraction.

24. The method of claim 23 wherein the duration of the individual pacing pulses averages less than 0.5 msec.

25. The method of claim 24 wherein the duty cycle of said individual pulses is at least 20%.

26. The method of claim 24 wherein the amplitudes of said series of individual pacing pulses rise from a first amplitude to a second amplitude.

27. The method of claim 14 wherein the pacing and background stimuli are delivered through electrodes whose configurations are different during the pacing and background stimulation intervals so that the background stimuli are, for the most part, not delivered through the chest but the pacing stimuli are delivered through the chest.

28. The method of claim 27 wherein one electrode is applied to either side of the chest, and the electrodes each comprise
    a first electrical terminal for making a connection to an external source of electrical current,
    a second electrical terminal for making a connection to an external source of electrical current,
    a first skin-contacting region electrically connected to said first terminal of the electrode, and
    a second skin-contacting region electrically insulated from said first region and spaced laterally from said first region and electrically connected to said second terminal of the electrode, and wherein
    the background stimuli are passed between the first and second skin-contacting regions of the same electrode, and the pacing stimuli are passed between from one electrode to the other electrode.

29. The electrodes of claim 28 wherein said first region laterally surrounds said second region.

* * * * *

UNITED STATES PATENT AND TRADEMARK OFFICE
CERTIFICATE OF CORRECTION

PATENT NO. : 5,205,284
DATED : April 27, 1993
INVENTOR(S) : Gary A. Freeman

It is certified that error appears in the above-indentified patent and that said Letters Patent is hereby corrected as shown below:

On the title page, item [56] References Cited, under OTHER PUBLICATIONS, the W.G.S. Stephens reference, "pp. 49-61" should be --pp. 47-51--

Col. 5, line 63, "skincontacting" should be --skin-contacting--.

Signed and Sealed this

Twenty-second Day of March, 1994

Attest:

BRUCE LEHMAN

*Attesting Officer*      *Commissioner of Patents and Trademarks*